United States Patent [19]

Petty-Weeks

[11] Patent Number: 4,661,211
[45] Date of Patent: Apr. 28, 1987

[54] GAS DETECTION WITH THREE-COMPONENT MEMBRANE AND SENSOR USING SAID MEMBRANE

[75] Inventor: Sandra Petty-Weeks, Naperville, Ill.

[73] Assignee: UOP Inc., Des Plaines, Ill.

[21] Appl. No.: 753,477

[22] Filed: Jul. 10, 1985

[51] Int. Cl.$^4$ .............................................. G01N 27/58
[52] U.S. Cl. .................................. 204/1 T; 204/424; 204/426; 204/427
[58] Field of Search ................ 204/1 T, 1 S, 421, 424, 204/425, 426, 427, 428, 429; 429/192, 213

[56] References Cited

U.S. PATENT DOCUMENTS

| | | | |
|---|---|---|---|
| 3,265,536 | 8/1966 | Miller et al. | 136/86 |
| 3,276,910 | 10/1966 | Grasselli et al. | 136/86 |
| 3,727,058 | 4/1973 | Schrey | 204/425 X |
| 4,024,036 | 5/1977 | Nakamura et al. | 204/129 |
| 4,040,929 | 8/1977 | Bauer et al. | 204/195 |
| 4,179,491 | 12/1979 | Howe et al. | 423/253 |
| 4,306,774 | 12/1981 | Nicolson | 350/357 |
| 4,324,760 | 4/1982 | Harris | 422/98 |
| 4,324,761 | 4/1982 | Harris | 422/98 |
| 4,373,375 | 2/1983 | Terhune et al. | 73/19 |
| 4,500,667 | 2/1985 | Polak et al. | 524/406 |
| 4,560,444 | 12/1985 | Polak et al. | 204/1 T |

OTHER PUBLICATIONS

Lundsgaard, J. S., et al, "A Novel Hydrogen Gas Sensor Based on Hydrogen Uranyl Phosphate," *Solid State Ionics*, 7 (1982), 53–56, North Holland Publishing Company.

"Hydrogen Detector Uses Silver–Palladium Probe," *Platinum Metals Review*, vol. 27, Jan. 1983, No. 1, p. 8.

MacIntyre, J. R. et al, "A Thin-Film Hydrogen Sensor," *Instrumentation Technology*, Aug., 1972, p. 29.

*Primary Examiner*—G. L. Kaplan
*Attorney, Agent, or Firm*—Thomas K. McBride; John F. Spears, Jr.; Richard J. Cordovano

[57] ABSTRACT

Apparatus and method for detecting and measuring hydrogen and gaseous compounds capable of dissociating into or combining with hydrogen ions using a solid electrolyte concentration cell. A novel solid electrolyte membrane is used which comprises a three-component blend prepared by admixing an organic polymer or copolymer, such as poly(vinyl alcohol), with an inorganic compound, such as a phosphoric acid, and an organic compound selected from a group of polymers and copolymers having monomer units containing nitrogen, oxygen, or sulfur atoms, such as poly(vinyl pyrrolidone), in a mutually miscible solvent. A reference gas or a solid reference substance is used. For increased strength, a membrane may be composited with or attached to a porous support.

29 Claims, 5 Drawing Figures

GAS DETECTION WITH THREE-COMPONENT MEMBRANE AND SENSOR USING SAID MEMBRANE

FIELD OF THE INVENTION

This invention relates to electrochemical measurement and detection. More specifically, it relates to the use of a novel solid electrolyte and a catalyst in detecting the presence of hydrogen or gases capable of dissociating to yield or combine with hydrogen ions, including oxygen, and measuring the quantity present. The solid electrolyte may be formed by blending an inorganic compound, an organic polymer or copolymer, and an organic compound selected from a group of polymers and copolymers having monomer units containing nitrogen, oxygen, or sulfur atoms, or by compositing a membrane comprising these components with a porous support. This invention also involves the use of a reference substance in solid form in place of a reference substance in gaseous form.

INFORMATION DISCLOSURE

U.S. Pat. No. 4,500,667 (Polak and Beuhler) describes proton conducting membranes.

U.S. Pat. No. 4,024,036 (Nakamura et al.) describes a proton permselective solid state member capable of exhibiting ionic conductivity.

U.S. Pat. Nos. 3,265,536 (Miller et al.), 4,306,774 (Nicholson), 3,276,910 (Grasselli et al.), and 4,179,491 (Howe et al.) deal with substances capable of conducting hydrogen ions.

An article by Lundsgaard et al. (Solid State Ionics 7, 1982, North-Holland Publishing Co.) describes experiments done using a substance which conducts hydrogen ions.

A hydrogen detector using more complex methods than that of the invention may be seen in U.S. Pat. No. 4,373,375 (Terhune et al.) and on p. 8 of *Platinum Metals Review*, January 1983, produced by Johnson Matthey, London. Three references showing hydrogen detectors which use an entirely different principle than the present invention are U.S. Pat. Nos. 4,324,760 and 4,324,761 (Harris) and an article on p. 29 of the August, 1972, *Instrumentation Technology*.

U.S. Pat. No. 4,040,929 (Bauer et al.) shows the use of a solid reference in an oxygen sensor.

BRIEF SUMMARY OF THE INVENTION

The present invention provides methods and apparatus for detecting gaseous hydrogen, hydrogen ion, dissociable hydrogen compounds, and compounds capable of combining with hydrogen ion, in order to indicate the presence or absence of these substances and, where desired, provide quantitative information on the amount present.

A novel three component solid electrolyte membrane is used in the present invention. We have discovered that a macroscopically homogeneous thin film polymer-blend membrane may be fabricated from an admixture of an inorganic compound, such as sulfuric acid or a phosphoric acid, with an organic polymer or copolymer and an organic compound selected from a group of polymers and copolymers having monomer units containing nitrogen, oxygen, or sulfur atoms, where the three components are at least partially compatible. This membrane is capable of acting as a proton conductor in a hydrogen detector where molecular hydrogen is converted into protons on one side of the membrane, protons are then transported through the membrane, and protons are recombined with electrons to form molecular hydrogen on the other sde. The membrane is also useful in detection of gases capable of dissociating into or combining with hydrogen ions.

In addition, the composition of matter utilized for said membrane may be composited on a porous support to form a composite membrane which possesses increased strength as well as being a protonic conductor. Examples of material used for such porous support include glass cloth, polysulfone, and ceramics.

The invention utilizes a concentration cell whose electrolyte is said membrane or composite membrane. A membrane is mounted in a sample cell or membrane housing having a sample gas chamber and a reference chamber, which chambers are separated by a partition comprising the membrane. The sample gas chamber contains the gas sample of interest, which must include a component capable of dissociating to form hydrogen ions or capable of combining with hydrogen ions. In the other chamber is a reference gas whose composition is known or a solid reference substance which exhibits a substantially constant known hydrogen partial pressure during use of the invention. Molecular transport through the membrane should be sufficiently slow so that gases will not mix by diffusing through it.

A catalytic agent for promotion of dissociation or combination is in intimate contact with the membrane on the sample gas side. Catalytic agent is also provided in a like manner on the reference side. It is not necessary that the same catalytic agent be used on both sides. Means for forming electrical contact and transferring electrons to and from an external circuit are provided on each side of the electrolyte in intimate contact with catalytic agent. The cell EMF is measured across said means for forming electrical contact and provides an indication of the presence of hydrogen or gases capable of combining with it in the sample gas and/or a quantitative measure of the amount of such which is present.

The method of the invention may be summarized as a method for detection, in a gas sample, of a gaseous component which is capable, in the presence of a catalytic agent, of dissociating to yield hydrogen ions or of combining with hydrogen ions, such method comprising contacting said gas sample with a first surface of a thin film polymer-blend membrane and detecting EMF between means for forming electrical connection with two separate portions of a catalytic agent effective to promote dissociation and combination, where a first portion of catalytic agent is in contact with said first surface and a second portion of catalytic agent is in contact with a second surface of said membrane, which membrane isolates said gas sample from a reference substance and has said second surface exposed to the reference substance, said membrane comprising a blend of three components, which components are an organic polymer or copolymer, an inorganic compound selected from a group consisting of phosphoric acids, sulfuric acid, heteropoly acids, and salts of heteropoly acids, and an organic compound selected from a group of polymers and copolymers having monomer units containing nitrogen, oxygen, or sulfur atoms, which organic compound is compatible with said inorganic compound and said organic polymer.

A calculating device may be used to automatically calculate concentrations, or calculation may be accomplished manually. This device may receive input from a temperature probe, or temperature may be entered manually for use in the calculation. Temperature of the gas or gases and/or the membrane housing may be controlled at a pre-established value. The catalytic agent may be platinum, palladium, or alloys thereof. The catalytic agent may be electrically conductive. Where temperature of the sample gas is too high or low for effective detection, it may be adjusted before the gas is contacted with the electrolyte element. It may be necessary to adjust the concentration, in a known manner, of sample gas contacting the membrane in order to achieve effective detection.

BACKGROUND OF THE INVENTION

The present invention utilizes a solid electrolyte sensor for detection of certain gases. The Nernst equation describes the behavior of sensing devices using solid electrolytes. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressures as follows:

$$EMF = E_o + (RT/nF) \ln (P_2/P_1),$$

where R is the gas constant, T is absolute temperature, F is the Faraday constant, $E_o$ is the standard oxidation-reduction potential difference, EMF is electromotive force, and n is the number of electrons per molecule of product from the overall cell reaction.

If the system described by the above equation behaves nonideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The rate of dissociation can be calculated by means of the equilibrium constant for the dissociation reaction.

The magnitude of EMF produced is generally in accordance with the parameters discussed herein: the Nernst equation and, where applicable, the dissociation equilibrium constant. However, required practice in measuring concentration is to periodically calibrate the measuring apparatus by use of samples whose composition is known. Thus, exact adherence to theoretical relationships is not required of commercially used methods and apparatus. The primary commercial requirement is repeatability.

We have discovered that a macroscopically homogeneous thin film polymer-blend membrane may be fabricated by admixing the organic and inorganic components discussed herein. Substances which are permeable by gases in a selective manner are known and utilized in a variety of applications. A membrane formed in accordance with the present disclosure is substantially impermeable to ions and gases, including hydrogen gas, but does allow hydrogen ions to pass through it. For background information relating to the principles of the present invention, reference may be made to the book *Solid Electrolytes and Their Applications*, edited by Subbarao, Plenum Press, 1980.

Low mechanical strength has been a common problem when attempting to apply permselective membranes. The present invention provides a membrane whose mechanical strength is increased by compositing it with other materials, but whose desirable properties are not lost as a result of doing so.

Also used in the present invention is a solid substance which is a substitute for a reference gas, which reference gas is one of the two media mentioned above in the discussion of the Nernst equation. It is highly desirable to use a solid reference substance which requires only periodic replacement instead of maintaining a continuous reference gas flow, or in appropriate situations, maintaining a sealed chamber of reference gas. The reference substance is in intimate contact with the catalytic agent on the reference side of the membrane. One substance may serve as both reference substance and catalytic agent.

DETAILED DESCRIPTION OF THE INVENTION

Figure 1:
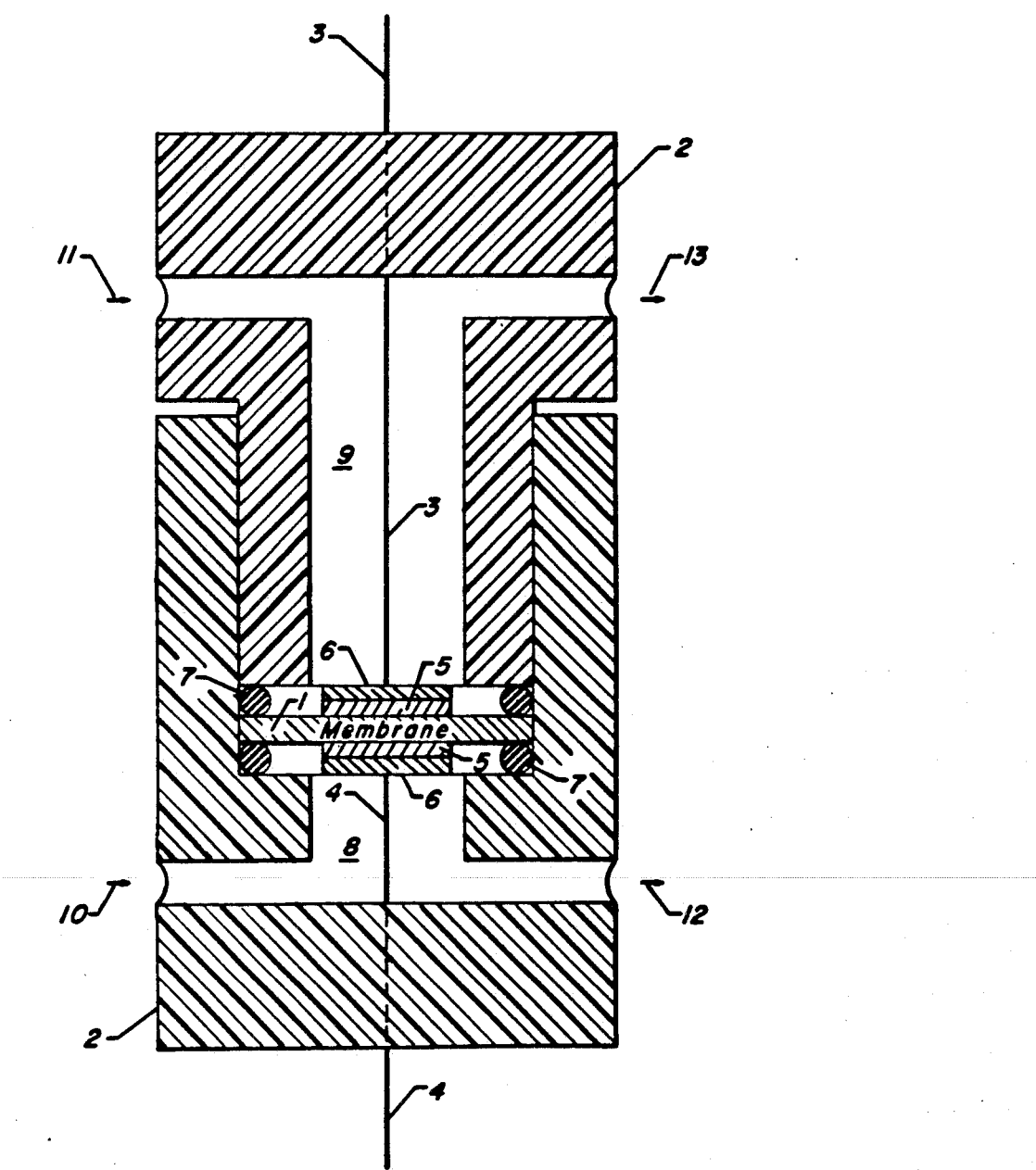
FIG. 1 is a schematic representation, in cross-section, of a test sensor similar to that used in initial proof of principle experimentation. The drawing is not to scale.

It has now been discovered that a useful blend of components may be obtained by admixing certain organic polymeric compounds with particular inorganic compounds, such as certain inorganic acids or salts thereof, and with certain organic compounds selected from a group of polymers and copolymers having monomer units containing nitrogen, oxygen, or sulfur atoms. The resulting composition of matter is formed into a macroscopically homogeneous thin film membrane which may be utilized in gas detection systems. The utility of these membranes in gas detection devices is due in part to the fact that the membranes will possess a high protonic conductivity, especially at room or ambient temperature.

Usually, high ionic conductivity is observed in polymer complexes only when the temperature is above their glass transition temperature (Tg), that is, above the temperature at which the substance changes from a solid to a liquid (the melting point of a polymer is usually above its glass transition temperature). Indications of the change of a polymer from solid to liquid are abrupt changes in certain properties, such as coefficient of expansion and heat capacity. The polymer-blend compositions of the present invention exhibit high protonic conductivity at temperatures well below the observed glass transition temperatures of the individual homopolymers. A device utilizing an ion-conducting polymer must operate below the Tg of the polymer; the polymer is not usable at higher temperatures due to loss of strength, tackiness, etc. A polymer-blend of the present invention exhibited two glass transition temperatures, which are attributable to the polymers but occur at different values than the glass transition temperatures determined for each polymer when it is not mixed with any other substance. In addition, at a relatively low temperature, a second order transition is observed; this is attributable to the inorganic compound. Thus, it may be appreciated that there is a degree of interaction between the components, that is, at least some chemical interaction exists between the components.

A distinct advantage which is possessed by the polymer-blend membranes of the present invention over other organic-inorganic blend membranes is that these membranes possess low resistivities (resistance times area divided by thickness), which are four to five orders of magnitude less than certain other organic-inorganic polymer blends. In using a gas sensor of the type of the present invention, it is necessary to measure the output voltage. When utilizing a membrane of the instant invention, it will be possible to use a voltage measuring device of lower impedance. Use of such a device will result in a simplified and lower cost electronics package for a commercial hydrogen sensor. A voltmeter should have an impedance (AC resistance) at least 3 orders of magnitude greater than that of the system in which it is used for measurement; high impedance voltage measuring devices are more costly than those of low impedance. In addition, a device with reduced impedance is less sensitive to electromagnetic interference than a high impedance device. This permits the device to be located in an electrically noisy environment without adversely affecting its performance.

The membrane comprises a blend of an organic polymer or copolymer, one of certain inorganic compounds, and an organic compound selected from a group of polymers and copolymers having monomer units containing nitrogen, oxygen, or sulfur atoms, which organic compound is at least partially compatible with the inorganic compound and organic polymer.

Examples of organic polymers which may be employed as one component of the blend of the present invention will include polymers and copolymers of vinyl alcohol, vinyl fluoride, ethylene oxide, ethylimine, ethylene glycol, cellulose acetate, vinylmethylethyl ether, phenol formaldehyde resins, etc.

The inorganic compound is selected from a group consisting of a phosphoric acid, sulphuric acid, heteropoly acids, or salts of heteropoly acids. Examples of phosphoric acids which may be employed will include hypophosphoric acid, metaphosphoric acid, orthophosphoric acid, pyrophosphoric acid, polyphosphoric acid, etc. The sulfuric acid which is employed will comprise an aqueous sulfuric acid which may contain from about 10% to about 40% sulfuric acid in the aqueous solution. Examples of heteropoly acids or salts thereof which may be employed as a component of the organic-inorganic blend which may be used to form a membrane will possess the generic formula:

$$A_m(X_xY_yO_z) \cdot nH_2O$$

in which X is selected from the group consisting of boron, aluminum, gallium, silicon, germanium, tin, phosphorus, arsenic, antimony, bismuth, selenium, tellurium, iodine, and the first, second, third and fourth transitional metal series, said series including scandium, yttrium, lanthanum, actinium, titanium, zirconium, hafnium, vanadium, niobium, tantalum, chromium, molybdenum and tungsten, Y is different from X and is selected from the first, second, third, or fourth transitional metal series, A is selected from the group consisting of hydrogen, ammonium, sodium, potassium, lithium, rubidium, cesium, beryllium, magnesium, calcium, strontium and barium, m is an integer of from 1 to 10, y is an integer of from 6 to 12 based on x taken as 1, z is an integer of from 30 to 80 and n is an integer of from 3 to 100.

Specific examples of these compounds will include dodecamolybdophosphoric acid (DMPA), ammonium molybdophosphate, sodium molybdophosphate, potassium molybdophosphate, lithium molybdophosphate, calcium molybdophosphate, magnesium molybdophosphate, dodecatunstophosphoric acid, ammonium tungstophosphate, sodium tungstophosphate, potassium tungstophosphate, lithium tungstophosphate, calcium tungstophosphate, magnesium tungstophosphate, dodecamolybdosilicic acid, ammonium molybdosilicate, sodium molybdosilicate, potassium molybdosilicate, lithium molybdosilicate, calcium molybdosilicate, magnesium molybdosilicate, dodecamolybdogermanic acid, ammonium molybdogermanate, sodium molybdogermanate, potassium molybdogermanate, lithium molybdogermanate, calcium molybdogermanate, magnesium molybdogermanate, hexamolybdotelluric acid, ammonium molybdotellurate, sodium molybdotellurate, potassium molybdotellurate, lithium molybdotellurate, calcium molybdotellurate, magnesium molybdotellurate, dodecatungstosilicic acid, ammonium tungstosilicate, sodium tungstosilicate, potassium tungstosilicate, lithium tungstosilicate, calcium tungstosilicate, magnesium tungstosilicate, etc.

The third component of the thin film polymer blend membrane of the present invention is an organic compound selected from a group of polymers and copolymers having monomer units containing nitrogen, oxygen or sulfur atoms, which organic compound is at least partially compatible with the aforementioned inorganic compounds and organic polymers and will include poly(ethyloxazoline), poly(vinyl sulfonic acid), poly(vinyl pyridine), poly(vinyl pyrrolidene), poly(vinyl pyrrolidone), polyimide, poly(acrylamide), etc. It is also contemplated within the scope of this invention that polymers of other organic compounds containing a mixture of nitrogen, oxygen and sulfur atoms such as poly(vinyl-substituted furans) etc. may also be employed, although not necessarily with equivalent results. It is desirable to select a compound which has a relatively high heat distortion temperature in comparison to the other components of the blend and is relatively hygroscopic. It is also desirable that this third component be at least partially miscible with the other components.

It is to be understood that the aforementioned listing of inorganic compounds, organic polymers, and organic compounds are only representative of the class of compounds which may be employed in formulating the inorganic-organic blends of the present invention, and that this invention is not necessarily limited thereto.

The novel compositions of matter used in the present invention are prepared by admixing the three components of the blend in a mutually miscible solvent at solution conditions for a period of time sufficient to form the desired blend. In the preferred membrane the mutually miscible solvent which is employed to dissolve the components comprises water, although it is contemplated within the scope of this application that any other mutually miscible solvent, either inorganic or organic in nature may also be employed. The mixing of the three components of the composition of matter may be effected at solution conditions which will include a temperature in the range of from about ambient (20°–25° C.) up to the boiling point of the mutually miscible solvent which, for example, in the case of water is 100° C. As an example, poly(vinyl pyrrolidone), poly(vinyl alcohol), and orthophosphoric acid may be placed in a flask and dissolved in water which has been heated to 100° C. The blend is cast upon a suitable casting surface which may consist of any suitable material sufficiently smooth in nature so as to provide a surface free of any defects which may cause imperfections on the surface of the membrane. Examples of suitable casting surfaces may include metals such as stainless steel, aluminum, etc., glass, polymer or ceramics. After casting the solution upon the surface, the solvent is then removed by any conventional means including natural evaporation or forced evaporation by the application of elevated temperatures, whereby said solvent is evaporated and the desired membrane comprising a thin film of the polymeric blend is formed. The thickness of the film can be controlled by the amounts of the various components of the blend which are present in the reaction mixture or by the depth of the casting vessel. The thin film organic-inorganic blend which is prepared according to the process of the present invention will possess a thickness which may range from about 0.1 to over 500 microns and preferably from about 20 to about 60 microns.

The amounts of inorganic compound, organic polymer or copolymer, and organic compound used in the blend may vary over a relatively wide range. For example, the inorganic compound which comprises a phosphoric acid, sulfuric acid, heteropoly acid or salts thereof may be present in the blend or membrane in a range of from about 1 to about 75 weight percent (preferably 30 to 60), the organic polymer may be present in the blend or membrane is a range of from about 1 to about 49 weight percent, and the organic compound containing a nitrogen atom, etc., may be present in the blend or membrane in a range of from about 1 to about 49 weight percent. Whenever a composition is expressed herein, it is to be understood that it is based, in the case of polymers, on the monomer repeat unit.

Some representative examples of a thin film polymer blend membrane which may be prepared will comprise orthophosphoric acid-poly(vinyl alcohol)-poly(vinyl pyrrolidone), pyrophosphoric acid-poly(vinyl alcohol)-poly(vinyl pyrrolidone), sulfuric acid-poly(vinyl alcohol)-poly(ethyloxazoline), dodecamolybdophosphoric acid-poly(vinyl alcohol)-poly(ethyloxazoline), dodecatungstophosphoric acid-poly-(vinyl alcohol)-poly(acrylamide), dodecamolybdosilicic acid-poly(vinyl alcohol)-poly(acrylamide), ammonium molybdophosphate-poly(vinyl fluoride)-poly(vinyl pyrrolidone), orthophosphoric acid-poly(vinyl alcohol)-poly(vinyl pyrrolidene), pyrophosphoric acid-poly(vinyl alcohol)-poly(ethyloxazoline), sulfuric acid-poly(vinyl alcohol)-polyimide, dodecamolybdophosphoric acid-poly(vinyl alcohol)-poly(vinyl pyrrolidone), dodecatungstophosphoric acid-poly(vinyl alcohol)-poly(ethyloxazoline), ammonium molybdophosphate-poly(vinyl alcohol)-poly(vinyl pyrrolidone), orthophosphoric acid-poly(vinyl alcohol)-poly(acrylamide), sulfuric acid-poly(ethylene oxide)-poly(acrylamide), dodecatungstophosphoric-acid-poly(vinyl alcohol)-poly(vinyl sulfonic acid), and ammonium molybdosulfate-cellulose acetate-poly(vinyl sulfonic acid).

It is to be understood that the aforementioned list of polymer blends is only representative of the class of polymer blended membranes which may be prepared and that the invention is not necessarily limited thereto.

It will be helpful in gaining an understanding of the invention to examine initial proof of principle experimentation. The information presented in regard to this experimentation is not meant to limit the scope of the invention in any way.

Three stock solutions were prepared: 10 grams of poly(vinyl alcohol) having a molecular weight of 133,000 was dissolved in 500 ml of deionized water, 5 grams of poly(vinyl pyrrolidone) having a molecular weight of 40,000 was dissolved in 250 ml of deionized water, and 14.7 grams (10 ml) of 85% (by wt.) orthophosphoric acid was dissolved in 100 ml of deionized water. To prepare a novel polymer blend membrane of the preent invention, 12.5 ml (0.25 gram) of stock poly(vinyl alcohol) solution, 6.4 ml (0.129 gram) of stock solution of poly(vinyl pyrrolidone) and 1.5 ml (0.219 gram) of stock solution of orthophosphoric acid were thoroughly admixed, the mole ratio of the resulting blend being 5:1:2 moles of poly(vinyl alcohol) to poly(vinyl pyrrolidone) to orthophosphoric acid. The solution was then poured into an evaporation dish and the water was allowed to evaporate at room temperature for a period of 16 hours. The resulting film was transparent and possessed a thickness of about 63 microns.

This thin film membrane was cut into a disc having a 1" diameter to form membrane 1 of FIG. 1 and platinum was sputter-deposited onto each side of the disc for a period of about 5 minutes per side. The platinum deposits each had a thickness of about 400 Angstroms and an area of about 1.5 square cm. Deposition was accomplished by means of a Hummer II sputter deposition system supplied by Technics Co. A biased screen between the target and film was used to reduce the electron flux to the membrane. There are many alternative methods which could have been used to form the platinum deposits, such as thermal evaporation or deposition by means of an ink. The porous structure of sputter-deposited catalytic agent is helpful in facilitating spillover of hydrogen ions onto the membrane, but such structure is not required.

Referring to FIG. 1, membrane 1, or disc 1, was mounted in test fixture 2, which may also be referred to as a sample cell, membrane housing, or test sensor. The above-mentioned platinum deposits 5 served as catalytic agent to promote dissociation and reassociation or combination of hydrogen. Electrical connection was made to the platinum through copper platens 6, which were held in place by springs (not shown) extending between the platens and interior surfaces of the sample cell. Platens 6 did not cover the entire surface of the catalytic agent, though FIG. 1 shows this to be the case. Note that when the catalytic agent is electrically conductive and not discontinuous, electrical contact need be made only at one point. However, catalytic agent need not be electrically conductive. Wire leads 3 and 4 extended from the platens out of the test fixture through means for sealing against gas leakage (not shown). Leads 3 and 4 were connected to EMF and current detection means (not shown). Membrane 1 was sealed into test fixture 2 by O-rings 7 so that there were no gas leakage paths between test gas chamber 8 and reference gas chamber 9. Tubing (not shown) was connected at the gas inlets as denoted by arrows 10 and 11 to provide gas flow into chambers 8 and 9 and was also connected to the gas outlets as denoted by arrows 12 and 13 to conduct gas away from the chambers. Gas-containing cylinders and gas flow control apparatus (not shown) were used to provide gas to test the sensor of fixture 2 in accordance with the herein described experiments. Several cylinders of hydrogen/nitrogen gas mixtures were purchased; an analysis (which was not checked) of the contents was supplied with each cylinder.

Gas flows were established through the chambers of the sample cell with both chamber pressures at about one atmosphere, since the chambers were vented directly to atmosphere by means of a short length of tubing. One flow was pure hydrogen (hydrogen partial pressure of 1.0 atm.) and the other was alternated between pure hydrogen and a 10% by volume mixture of hydrogen in nitrogen (hydrogen partial pressure of 0.1 atm.). The voltage across wires 3 and 4 was recorded by means of a standard laboratory strip chart recorder. When the flow to one chamber was alternated every 20 minutes, the voltage versus time plot was a substantially perfect square wave form. Voltage varied consistently between 0.0 millivolts and 29.1 mv. Response was Nernstian; the calculated voltage is also 29.1 mv (at a room temperature of about 22° C.). Note that this is open circuit voltage. Voltage deviation from theoretical was less than about 1%.

When the gases (100% hydrogen and 10% hydrogen) were continuously flushed through the cell with no alternations for a period of 24 hours, the delta voltage remained at 29.1 mv for the duration of the test period. Upon connection of an ammeter to wires 3 and 4, the measured current was 0.0133 ma at the beginning of the test period and 0.0019 ma after 24 hours. The decrease in current flow over the test period is due to removal of water from the membrane, since the membrane was not completely dry. Current flow stabilized at the latter value. The resistance of the membrane was measured when 100% hydrogen was flowing through both chambers of the sample cell. For a 63 micron thick membrane with 1.5 cm$^2$ of platinum on each surface, the resistivity was calculated from EMF and current data to be $3.7 \times 10^6$ ohm-cm. This applies to a membrane exposed to dry gas for 24 hours. When a membrane which was not completely dry was placed under test, the initial resistance was lower.

Other membranes prepared from the above-mentioned stock solutions were tested after sputter deposition of platinum. Voltage response was always Nernstian, but current flow varied. For example, a membrane was prepared by admixing 12.5 ml (0.25 gram) of the poly(vinyl alcohol) stock solution, 6.4 ml (0.13 gram) of the stock poly(vinyl pyrrolidone) solution and 1.0 ml (0.14 gram) of the stock phosphoric acid solution. The membrane had a mole ratio of 5:1:1.3 poly(vinyl alcohol) to poly(vinyl pyrrolidone) to phosphoric acid. The membrane was tested in a manner similar to that set forth above. Initial closed circuit current was $1.3 \times 10^{-4}$ ma; after 17 hours and 22 hours under test, it was $2 \times 10^{-5}$ ma, corresponding to a hydrogen flux of $1.9 \times 10^{-7}$ ft$^3$/ft$^2$-hr. Thickness of the membrane was 58 microns and resistivity was $3.8 \times 10^8$ ohm-cm.

Another membrane was prepared by admixing stock solutions of poly(vinyl alcohol), poly(vinyl pyrrolidone) and orthophosphoric acid in an amount sufficient to provide a molar ratio of 5:1:4 poly(vinyl alcohol) to poly(vinyl pyrrolidone) to orthophosphoric acid. The weight ratio was 30:16:54. The membrane was tested in a manner similar to that above. Initial closed circuit current was 0.022 ma; after 24 hours under test it was 0.016 ma and after 72 hours, it drifted to 0.015 ma. The latter value corresponds to a hydrogen flux of $1.4 \times 10^{-4}$ ft$^3$/ft$^2$-hr. Thickness of the meembrane was 80 microns and resistivity was $3.5 \times 10^5$ ohm-cm at 24 hours.

In addition to platinum, palladium may be deposited on membranes for use as catalytic agent. Nernstian voltage response will be observed when palladium is used. Other catalytic agents are available and known to those skilled in the art. The catalytic agent need not be electrically conductive; however, then the means for forming electrical connection must be in contact with the catalytic agent over a broad area to facilitate movement of electrons from sites of the catalytic agent to the electrically conductive substance or electrode. Alternatively, catalyst may be embedded in a conductive matrix. Areas of membrane which are not adjacent to catalytic agent are not effective in the invention. Hydrogen ions spill over from the catalytic agent to the membrane and then the protons move through the membrane.

Response time of a sensor was noted. When the 100% hydrogen and 10% hydrogen gas streams were alternated as described above, the time required for the voltage to change between steady state values was approximately 6 seconds. It should be noted tht the sample cell used is not necessarily designed for quick response.

Sensors utilizing the present membrane have not yet been tested with sample gases containing small amounts of potential poisons. However, it is believed that the present membranes will exhibit the same behavior as certain other membranes which were tested. In these tests, addition of carbon monoxide in an amount of about 0.1% by volume in a hydrogen sample gas stream with a 100% hydrogen reference gas stream caused a change in EMF indicative of a large reduction in hydrogen partial pressure. This apparent drop in hydrogen concentration was much larger than the expected drop due to the effect of dilution of sample gas with CO. This is likely due to the competition by CO with molecular hydrogen for adsorption sites on platinum. No interference with the hydrogen concentration measurements was detectable when 100 PPM by volume of CO was added to a sample gas stream. It is expected that the present invention cannot be used to measure the amount of hydrogen, or other gas, present in a sample gas which also contains significant amounts of CO, or other substances which interfere in the same manner, unless the amount of CO, or other substance, is known by other means or constant. The following potential poisons did not interfere with hydrogen concentration measurements made using the other membranes: hydrogen chloride (10 PPM), hydrogen sulfide (3%), carbon dioxide (100 PPM), membrane (3%), and butane (3%). All of the concentrations in sample gas shown in parenthesis are by volume.

Membranes of the present invention have been tested at temperatures ranging from minus 30° C. to plus 50° C. Nernstian behavior was observed though, of course, voltage varies with temperature. It may be possible to use these membranes at higher temperatures, but no tests have been conducted.

The above description of the invention has dealt with hydrogen detection. It is clear that any substance capable of dissociating in the presence of a catalyst to yield hydrogen ions may be detected in the same manner. An example is hydrogen chloride (using palladium or nickel catalyst if HCl is at room temperature). The Nernst equation applies in a manner similar to that described herein. The invention is also useful in detecting any gaseous component of a gas sample which is capable of combining with hydrogen ions. Oxygen may be used to illustrate this embodiment. Protons passing through the membrane from a reference gas chamber containing pure hydrogen will combine with oxygen in a sample gas and electrons from the external circuit (for example, wires 3 and 4 of FIG. 1) to form water, in contrast to a hydrogen detector, wherein hydrogen is formed. The Nernst equation is applicable; the $E_o$ term is not 0, as it is when the same substance is present on both sides of the membrane, and the partial pressure of oxygen to the one-half power times the partial pressure of hydrogen divided into the partial pressure of water replaces the analogous term of the equation. Hydrocarbons capable of hydrogenation or dehydrogenation may be objects of detection. Examples are cyclopentadiene, benzene, isoprene, cyclohexane, and isoamylene.

It is often desirable to avoid the use of a reference gas in the methods and apparatus of detection described herein. This may be accomplished by using a reference substance in the form of a solid. As discussed herein, it is necessary that a substance with a known partial pressure of hydrogen be used as a reference. It is also necessary that the reference partial pressure remains substantially constant as hydrogen is added to or removed from the reference substance.

Figure 3:
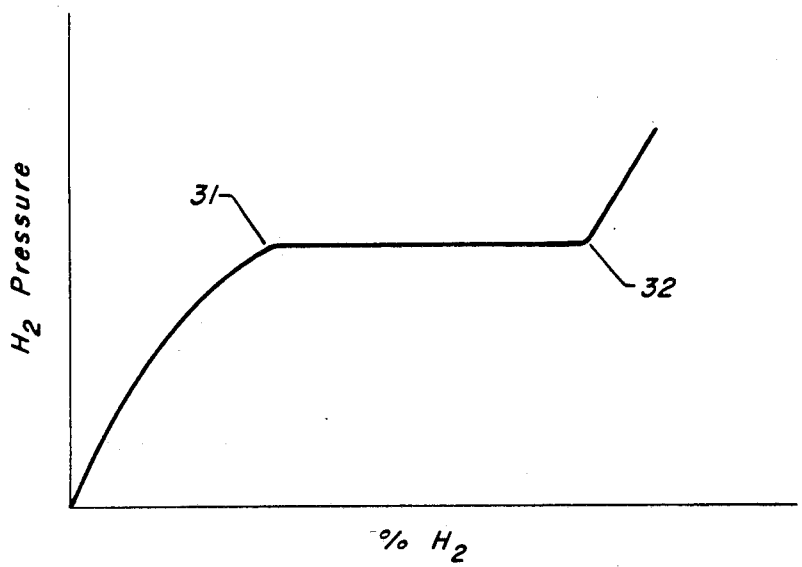
FIG. 3 is a portion of a phase diagram of a solid reference substance capable of use in an embodiment of the present invention, in which hydrogen partial pressure of the substance is plotted against the amount of hydrogen in the substance. If the plot were extended to larger amounts of hydrogen, several plateaus might appear.

In the sensor of the present invention, the EMF developed is an open circuit value. Thus, theoretically there are no electrons flowing in the external circuit to combine with protons passing through the membrane and therefore no change in reference hydrogen concentration. Of course, in actuality there is a small current flowing and reference hydrogen concentration is constantly changing. A reference substance must possess the characteristic of constant hydrogen partial pressure while hydrogen concentration changes. FIG. 3 depicts a portion of a phase diagram of a solid substance suitable for use as a reference substance in the present invention. For a sensor having a solid reference substance to function properly, the hydrogen concentration must lie on the plateau, or horizontal portion, of the curve of FIG. 3, the plateau lying between points 31 and 32. As the hydrogen content of the reference substance increases or decreases due to operation of the sensor, that is, as hydrogen, or other substance, forms from the protons which pass through the membrane and the electrons which flow in the external circuit, the point representing the reference substance moves along the plateau. However, as long as the point is on the plateau the hydrogen partial pressure remains constant and, therefore, the reference substance is useful. It can be seen that a particular reference substance has a limited life. Since the time required to change the hydrogen concentration beyond the limits represented by points 31 and 32 can easily be measured in months or years, the use of a solid reference is practical. Since the flow of protons through the membrane may be in either direction, hydrogen content of the solid reference substance may increase or decrease. When it passes above point 32 or below point 31, the reference substance must be replaced.

Metal hydrides are, in general, suitable for use as solid reference substances in this invention, since their phase diagrams are usually similar to that of FIG. 3. There may be several plateaus on one diagram, so that there is a choice of reference partial pressures while using one particular substance. Examples of metal hydrides include substances consisting of hydrogen and oxygen with tungsten, molybdenum, vanadium, or iridium, hydrogen-zirconium-nickel compounds, hydrogen-zirconium-platinum compounds, and compounds of hydrogen with platinum, palladium, zirconium, hafnium, vanadium, and niobium. Further examples comprise compounds of hydrogen and elements of atomic numbers of 3, 11, 12, 19 through 28, 37 through 48, 55 through 60, 62, 64, 72 through 78, 90, and 92.

The present membranes have not yet been tested with a solid reference substance. However, it is expected that the present membranes will exhibit the same behavior as certain other membranes which were tested. In proof of principle experimentation utilizing one of these other membranes, the apparatus of FIG. 2 was fabricated. Palladium layer 42 of approximately 1000 Angstroms thickness was sputter-deposited on substrate 41. The substrate used was alumina. Choices of substrate may be made from a wide variety of materials and are not a part of the invention. The palladium layer was moistened with DI water and a membrane 43 was placed over it. The membrane had a thickness of approximately 50 microns. Platinum layer 44 was sputter-deposited on membrane 43 to a thickness of approximately 400 Angstroms. Wires 45 and 46 were attached to platinum layer 44 and palladium layer 42. The wires were connected to voltmeter 47. In addition, switch 48 was provided in parallel with the voltmeter to complete an external circuit when desired.

The apparatus was exposed to hydrogen gas for about two hours, with switch 48 closed, to add hydrogen to palladium layer 42 to provide the reference substance. Hydrogen dissociated at platinum layer 44 and the protons passed through membrane 43 while the electrons from the dissociated molecules flowed through the external circuit consisting of wires 45 and 46 and switch 48. It is not necessary to form the reference substance in place in this manner; palladium hydride could have been deposited on the substrate. The palladium hydride served as both catalytic agent and reference substance.

Figure 2:
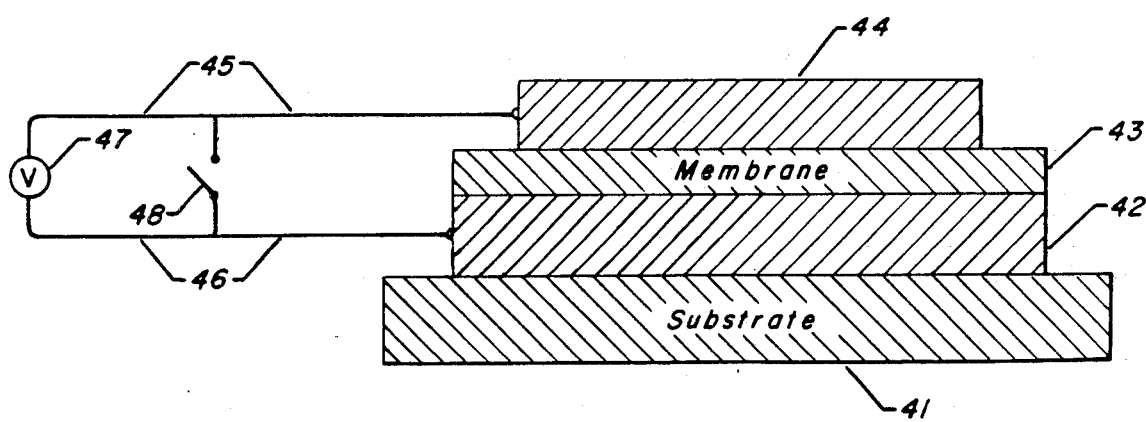
FIG. 2 is a schematic representation, in cross-section, of a test sensor which may be used in experimentation for the embodiment which utilizes a solid reference substance. It is not to scale.

The apparatus depicted in FIG. 2 is an example of a sample cell or membrane housing. The space adjacent to catalytic agent 44 comprises the sample gas chamber. The spaced occupied by reference substance 42 comprises the reference chamber. Membrane 43 comprises a substantially imporous partition separating the chambers. If it were desired to use a catalytic agent separate from the reference substance, catalytic agent would be depicted as a layer between the layers 42 and 43.

After completion of fabrication of the sensor, it was placed in a closed chamber and pure hydrogen gas was passed over the sensor. Switch 48 was open, since it is used only during fabrication of the sensor, i.e., during hydrogenation of the palladium. A valve in the outlet tubing from the closed chamber was partially closed to throttle hydrogen flow out of the chamber and increase chamber pressure. Voltages at various pressures were recorded and found to match values calculated using the Nernst equation.

The reference partial pressure of hydrogen which is used in the Nernst equation to determine EMF is easily calculated. For example, niobium hydride has a hydrogen partial pressure of approximately $10^{-6}$ atmospheres, as calculated by the relationship $$\tfrac{1}{2} \ln P = (A/RT) - (B/R),$$

where A=enthalpy between the two hydride phases expressed in kcal/gm-atom, B=entropy between the two hydride phases expressed in cal/gm-atom-°K., $P = P_2$ or $P_1$ as defined above, and R and T are as defined above.

Figure 4:
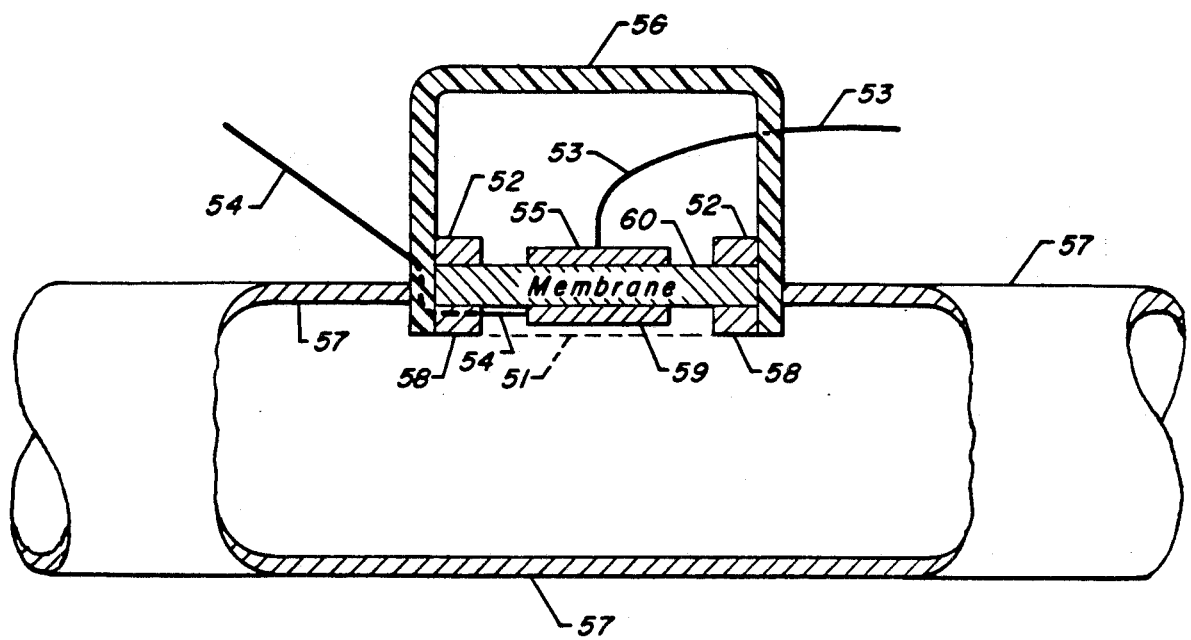
FIG. 4 depicts, in a sectional view, a sensor with a sealed reference chamber mounted on a pipeline. It is not to scale and has non-essential elements omitted.

It can be seen that a membrane mounted in a cell such as depicted in FIGS. 1 and 4 may be subjected to high differential pressures which may deform or burst the membrane. A composite membrane may be fabricated by casting a solution prepared as described above on a flexible porous support. A supported membrane assembly may be fabricated by attaching a membrane which is cast and dried as above to a rigid porous support. Attachment may be accomplished by moistening the surface of the membrane and support and pressing the moistened surfaces together. The moisture will evaporate.

It is contemplated that any porous substrate which possesses a structural strength greater than the thin film membrane may be employed. Some examples of these porous supports will include compounds such as glass cloth, polysulfone, cellulose acetate, polyamides, ceramics such as aluminaa, glass, porcelain, etc. which have been fabricated to process the necessary porosity. The amount of blend which is cast upon the flexible porous support will be that which is sufficient to form a thin film membrane having a thickness within the range herein set forth. After casting, the mutually miscible solvent such as water is removed by conventional means such as normal evaporation or forced evaporation by the application of external heat, application of vacuum, etc., and the desired membrane comprising the thin film blend composited on the porous support may be recovered and utilized in an appropriate gas sensor apparatus.

A polymer-blend similar to that of the present invention was prepared. After a period of time sufficient to form the blend had passed, the solution was stirred and poured onto the top of a fine glass cloth which was positioned in a standard Petri dish. The water was allowed to evaporate for a period of 48 hours and the resulting membrane composite comprising a thin film membrane composited on, or with, the glass cloth having a thickness of 95 microns was recovered. The composite membrane was cut into a circle having a 1" diameter and platinum electrodes 1 square cm in area were sputter-dispersed on each side of the membrane. The membrane was then placed in a sample housing similar to that of FIG. 1 for test. The sensor response was Nernstian. However, the resistivity was higher.

As an illustration of the greater structural strength of a polymer blend composited on a porous support when compared to unsupported membranes, reference may be made to previous work involving two component polymer blend membranes. Two polymer blend membranes were prepared. The polymer blend was prepared by dissolving 0.5 gram of poly(vinyl alcohol) having a molecular weight of 16,000 and 0.2 ml of orthophosphoric acid in boiling deionized water. The resulting blend was cast onto a glass cloth having a thickness of 30 microns. A second blend was prepared by admixing like proportions of poly(vinyl alcohol) and orthophosphoric acid and casting the resulting blend onto a Petri dish without a support. After removal of the solvent, the two membranes were recovered.

Each membrane was placed in a holder which enabled air pressure to be exerted against one side of the membrane while the other side was at atmospheric pressure. When exposed to 5 psig, the unsupported membrane burst at its center in less than 1 minute. At 2 psig another sample of unsupported membrane bulged and was permanently deformed. The composite membrane was subjected to various pressure levels in 5 psig increments with one minute hold time between increases in pressure. It burst at 35 psig, shearing at the edges of the test hole in the holder. The point of failure leads one to believe that holder design caused the shearing and that a higher burst pressure would be observed in a different holder.

As is common in many analysis instruments, the sample gas provided to a sensor may require conditioning in order to achieve effective detection. Of course, any particular matter and liquid droplets are removed. The extent of conditioning depends on the particular gas involved and its state. For example, an extremely hot gas must be cooled to a sufficiently low temperature so as not to degrade the apparatus by melting sensor components, including the membrane. A relatively cold gas may need to be heated to a temperature which promotes a reasonable response time of the apparatus. A related factor to be considered is the necessity for knowing the temperature for use in the Nernst equation. The temperature may be measured or the temperature may be maintained at a pre-established constant value. If the caibration gas temperature is maintained at the same value, the matter is simplified. Water vapor and/or other substances are often removed from or added to a sample gas stream. Other sample-conditioning techniques may be required. For example, in a situation where the concentration of the unknown substance is extremely large and capable of saturating the apparatus, the sample may be diluted by addition of a known amount of inert gas. The actual concentration of undiluted sample can then easily be calculated.

A detector may take many forms. A portable battery-operated unit may be used as a "sniffer" to detect the presence in the atmosphere of a particular gas due to leakage from a closed system. A detector may be permanently mounted in a particular location to detect leaks. When conditioning is not required, a detector may be fabricated for insertion directly into a process pipeline. When a gas sample must be conditioned, a small sidestream may be withdrawn from a process pipeline on a continuous or intermittent basis and passed through a sample gas chamber. A quantity of reference gas may be sealed into a reference gas chamber instead of providing a continuous flow.

Figure 5:
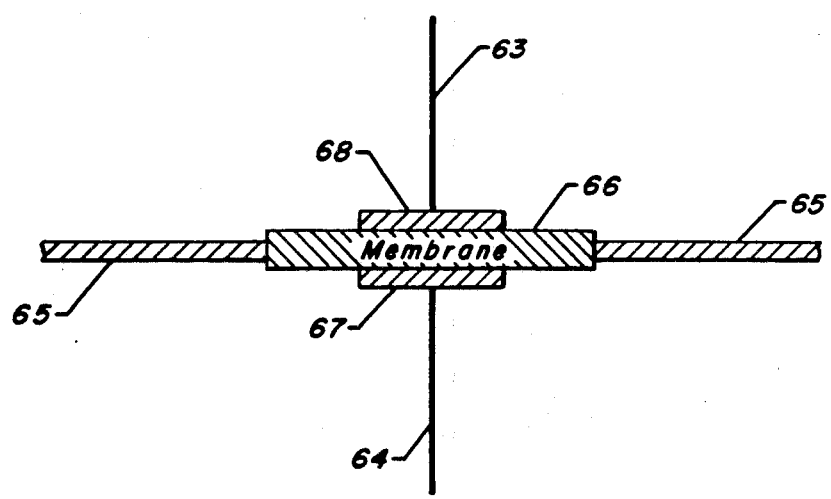
FIG. 5 depicts an embodiment of the invention, in a sectional view, in which a membrane is part of a partition separating a sample gas chamber from a reference chamber.

As used herein, the term "detection" includes not only sensing presence or absence of the detected substance, but measurement of the amount of substance present, either in order of magnitude or exact amounts. Gas sample refers to any portion of a gas which is the subject of detection. A gas sample may have only one component. Sample cell or membrane housing or test fixture refers to a housing or fixture which holds an electrolyte element and other required components. FIG. 5 depicts a membrane housing. Sensor is a general term denoting sensing apparatus, such apparatus comprising a membrane housing. Membrane or electrolyte element refers to an ion-conducting substance suitable for use as an electrolyte in the concentration cell of this invention which has been formed into a particular physical entity, either with or without additional substances, for use in the invention. Where an electrolyte element surface is referred to as in common with a gas or gas chamber, the meaning is the same as exposed to a gas or gas chamber and such reference does not preclude the presence of catalytic agent and electrodes at or covering the surface. Gas may diffuse through covering material. Sample gas chamber refers to any space in which gas which is the subject of detection exists. For example, a sample cell can form a part of a pipeline wall such that the gas flowing in the pipeline is the sample gas and the pipeline is the sample gas chamber. The term "gas" is used herein to include vaporized liquids regardless of boiling point characteristics of the substance. As used herein, miscible means capable of being mixed where there may only be a very small degree of solubility. As is familiar to those skilled in the art, the terms concentration and partial pressure are often used interchangeably; partial pressure expresses concentration. Compatible may be taken to mean that compatible compounds will form the polymer-blend composition of matter.

The design of sample cells, or detectors, or membrane housings, is well known. Many configurations are possible; FIG. 1 provides an example of one type. FIG. 4 depicts an embodiment of the invention where membrane housing 56 is mounted (attachment means not shown) in the wall of pipeline 57. Gas is present and may or may not be flowing in the pipeline. The sample gas chamber is the interior of the pipe adjacent to housing 56, while the reference chamber is defined by housing 56 and solid electrolyte membrane 60. Reference gas is sealed into the reference gas chamber; thus it is necessary to replace the reference gas at intervals upon its changing in concentration as a result of the cell reaction sufficiently to affect sensor results. It should also be noted that the membrane is not expected to be totally impermeable and that substances in addition to hydrogen ion may pass through it. Permeability experimentation has not been accomplished, except to the extent indicated herein. Alternatively, the reference chamber may contain a solid reference substance. Electrically conductive catalytic agent is present on both sides of membrane 60, as shown by reference numbers 55 and 59. Wire leads 53 and 54 extend outside the apparatus for connection to voltage detection means. Retaining rings 52 and 58 serve to hold membrane 60 in place at its perimeter (exact detail not shown). Screen 51 is provided to protect membrane 60 from the impact of large particles or objects. If a greater membrane surface area than that of FIG. 4 is desired, a detector may be fabricated in the form of a cylindrical probe for insertion into a pipeline. Membrane material may be placed over a perforated pipe which is sealed at one end. The interior of the perforated pipe is the reference gas chamber. It may be desirable to protect the membrane and catalytic agent by covering it with a porous substance through which sample gas can pass.

Referring to FIG. 5, an embodiment of the invention in which a membrane 66 serves as a part of partition 65 is shown. Partition 65 separates a sample gas chamber from a reference gas chamber. Catalytic agent 67 and 68 and wire leads 63 and 64 perform the functions discussed above.

I claim as my invention:

1. Apparatus for detection, in a gas sample, of a gaseous component which is capable, in the presence of a catalytic agent, of dissociating to yield hydrogen ions or of combining with hydrogen ions comprising:
   (a) a thin film polymer-blend membrane which comprises a solution blend of three components, which components comprise a component (1) selected from the group consisting of (i) an organic polymer selected from the group consisting of poly(vinyl alcohol), poly(vinyl fluoride), poly(ethylene oxide), polyethylimine, poly(ethylene glycol), cellulose acetate, polyvinylmethylethyl ether and phenol formaldehyde resins, and (ii) a copolymer having as a repeat unit one of the monomer units of the polymers of (i), (2) an inorganic compound selected from the group consisting of phosphoric acids, sulfuric acid, heteropoly acids, and salts of heteropoly acids, and (3) an organic compound selected from the group consisting of polymers and copolymers having monomer units containing nitrogen, oxygen, or sulfur atoms, which organic compound is compatible with said inorganic compound and said component (1), said organic compound being selected from the group consisting of poly(ethyloxazoline), poly(vinyl sulfonic acid), poly(vinyl pyridine), poly(vinyl pyrrolidene), poly(vinyl pyrrolidone), polyimide and poly(acrylamide);
   (b) a membrane housing comprising a sample gas chamber and a reference substance chamber separated by a partition comprising said membrane, said membrane having a first surface in common with the sample gas chamber and a second opposing surface in common with the reference substance chamber;
   (c) two separate portions of catalytic agent effective to promote dissociation and combination, a first portion in contact with said first surface of said membrane and a second portion in contact with said second surface of said membrane;
   (d) means for forming electical connection in operative contact with said catalytic agent at said first surface and with said catalytic agent at said second surface;
   (e) means for measuring EMF between said first and second surfaces;
   (f) means to supply sample gas to said sample gas chamber; and
   (g) means to provide an indication of the presence of hydrogen or of a gas capable of combining with hydrogen ions based on the measured EMF.

2. The apparatus of claim 1 further characterized in that said catalytic agent comprises a substance selected from a group consisting of platinum, palladium, and alloys thereof.

3. The apparatus of claim 1 further characterized in that said catalytic agent is electrically conductive.

4. The apparatus of claim 1 further characterized in that said catalytic agent is porous to said gaseous component.

5. The apparatus of claim 1 further comprising means to supply sample gas to said sample gas chamber and reference gas to said reference substance chamber.

6. The apparatus as set forth in claim 1 in which said inorganic compound is present in said blend in an amount in a range of from about 1 to about 75 weight percent, said organic polymer or copolymer is present in said blend in an amount in a range of from about 1 to about 49 weight percent, and said organic compound is present in said blend in an amount in a range of from about 1 to about 49 weight percent.

7. The apparatus as set forth in claim 1 in which said membrane possesses a thickness of from about 0.1 to about 500 microns.

8. The apparatus as set forth in claim 1 in which said blend is composited with a flexible porous support.

9. The apparatus as set forth in claim 8 in which said porous support comprises glass cloth.

10. The apparatus as set forth in claim 1 in which said membrane is attached to a rigid porous support.

11. The apparatus of claim 1 further characterized in that said reference substance chamber contains a reference gas.

12. The apparatus of claim 1 further characterized in that said reference substance chamber contains a reference substance in solid form, which reference substance is in contact with said second portion of catalytic agent and exhibits a substantially constant known hydrogen partial pressure during use of said detection apparatus.

13. The apparatus of claim 12 further characterized in that said reference substance is a metal hydride.

14. The apparatus of claim 12 further characterized in that a single substance serves as both reference substance and catalytic agent.

15. The apparatus of claim 12 further characterized in that said reference substance and said catalytic agent is palladium hydride.

16. The apparatus as set forth in claim 1 wherein said component (1) comprises poly(vinyl alcohol).

17. The method of claim 1 wherein said component (1) comprises poly(vinyl alcohol).

18. The apparatus as set forth in claim 1 wherein said component (2) comprises orthophosphoric acid.

19. The apparatus as set forth in claim 1 wherein said component (3) comprises poly(vinyl pyrrolidone).

20. A method for detection, in a gas sample, of a gaseous component which is capable, in the presence of a catalytic agent, of dissociating to yield hydrogen ions or of combining with hydrogen ions, such method comprising the steps of
(a) providing a three component polymer blend membrane which comprises a solution blend of (1) a component selected from the group consisting of (i) an organic polymer selected from the group consisting of poly(vinyl alcohol), poly(vinyl fluoride), poly(ethylene oxide), polyethylimine, poly(ethylene glycol), cellulose acetate, polyvinylmethylethyl ether and phenol formaldehyde resins, and (ii) a copolymer having as a repeat unit one of the monomer units of the polymers of (i), (2) an inorganic compound selected from the group consisting of phosphoric acid, sulfuric acid, heteropoly acids, and salts of heteropoly acids, and (3) an organic compound selected from the group consisting of polymers and copolymers having monomer units containing nitrogen, oxygen, or sulfur atoms, which organic compound is compatible with said inorganic compound and said component (1), said organic compound being selected from the group consisting of poly(ethyloxazoline), poly(vinyl sulfonic acid), poly(vinyl pyridine), poly(vinyl pyrrolidene), poly(vinyl pyrrolidone), polyimide and poly(acrylamide), said membrane including two separate portions of a catalytic agent effective to promote dissociation and combination, with a first portion of said catalytic agent being in contact with a first surface of said membrane and a second portion of said catalytic agent being in contact with a second opposing surface of said membrane,
(b) contacting said gas sample with said first surface of said membrane while isolating a reference substance on the opposing side of said membrane and exposing said reference substance to said opposing second surface of said membrane; and
(c) measuring EMF between said separate portions of catalytic agent during said contacting and determining the presence of said gaseous component in said gas sample.

21. The method of claim 20 further characterized in that said gaseous component is elemental hydrogen.

22. The method of claim 20 further characterized in that said gaseous component is elemental oxygen.

23. The method of claim 20 further characterized in that the concentration of said gaseous component in the gas sample is adjusted before the sample contacts said membrane.

24. The method of claim 20 further characterized in that the temperature of said gas sample and/or said reference substance is adjusted before said gas sample contacts said membrane.

25. The method of claim 20 further characterized in that said reference substance is in gaseous form.

26. The method of claim 20 further characterized in that said reference substance is in the form of a solid, which is in contact with said second catalytic agent portion and exhibits a substantially constant known hydrogen partial pressure during practice of said method for detection.

27. The method of claim 20 further characterized in that said membrane is comprised of poly(vinyl alcohol), poly(vinyl pyrrolidone), and orthophosphoric acid.

28. The method of claim 20 wherein said component (2) comprises orthophosphoric acid.

29. The method of claim 20 wherein said component (3) comprises poly(vinyl pyrrolidone).

* * * * *